United States Patent [19]

Thanawalla

[11] 4,161,949
[45] Jul. 24, 1979

[54] ASEPTIC CONNECTOR

[75] Inventor: Chandrakant B. Thanawalla, King of Prussia, Pa.

[73] Assignee: Pennwalt Corporation, Philadelphia, Pa.

[21] Appl. No.: 846,227

[22] Filed: Oct. 27, 1977

[51] Int. Cl.² .................................................. A61M 3/00
[52] U.S. Cl. ............................. 128/247; 128/214.2; 128/272.3
[58] Field of Search .................... 128/247, 272.3, 272.1, 128/214 D, 214.2, 218 M, 218 DA; 141/329, 311; 285/3, 260

[56] References Cited

U.S. PATENT DOCUMENTS

| 3,987,791 | 10/1976 | Chittenden et al. | 128/272.3 |
| 4,004,586 | 1/1977 | Christensen et al. | 285/260 X |
| 4,059,112 | 11/1977 | Tischlinger | 128/272.3 |

FOREIGN PATENT DOCUMENTS

| 2402310 | 7/1974 | Fed. Rep. of Germany | 128/272.3 |
| 2442856 | 11/1975 | Fed. Rep. of Germany | 128/272.3 |

*Primary Examiner*—John D. Yasko
*Attorney, Agent, or Firm*—Charles N. Quinn

[57] ABSTRACT

A connector for affecting aseptic juncture of two bodies for flow of fluid therebetween comprises a female element having a base, a conduit passing through the base, a cylindrical sheath extending from the base and concentrically spaced about a portion of the conduit, an annular exterior wall extending from the base a greater distance than the sheath and concentrically spaced thereabout and pellicular means for sealing the annular exterior wall at a position remote the base, with a male element telescopingly engageable with the female element and including a sole, a conduit passing through the sole and tubular means extending from the sole a greater distance than the conduit and concentrically spaced thereabout. Means are provided for retaining the male and female elements in telescoping engagement. Puncturable pellicular membranes at the extremities of the male and female elements maintain the element interiors in an aseptic condition until the membranes are ruptured when the male and female elements are joined.

10 Claims, 7 Drawing Figures

AXIAL DIRECTION

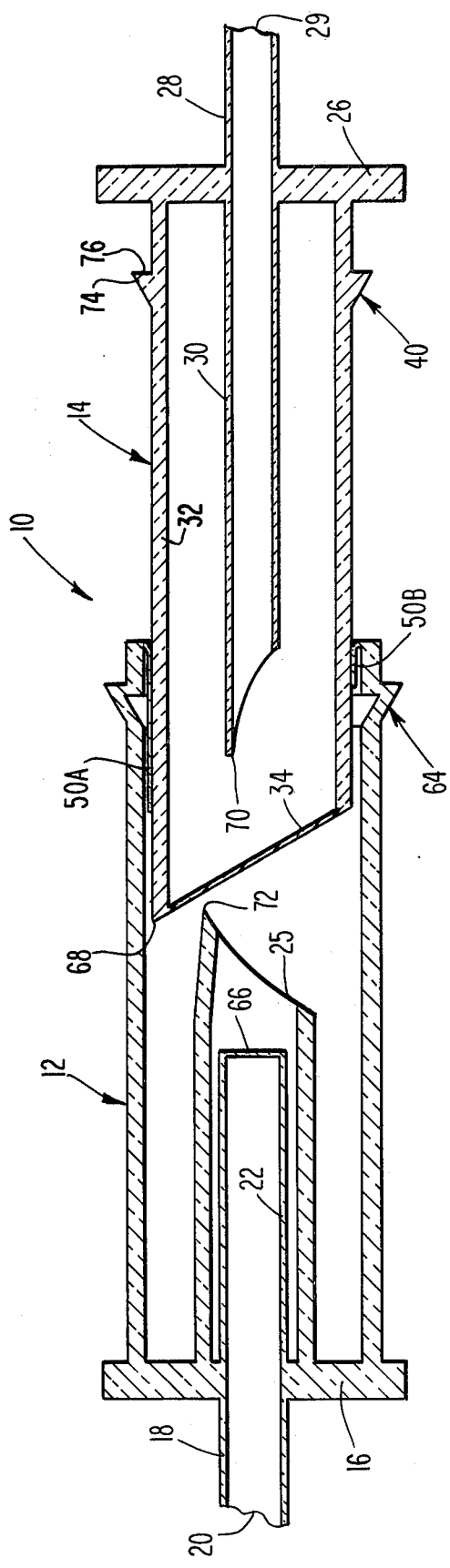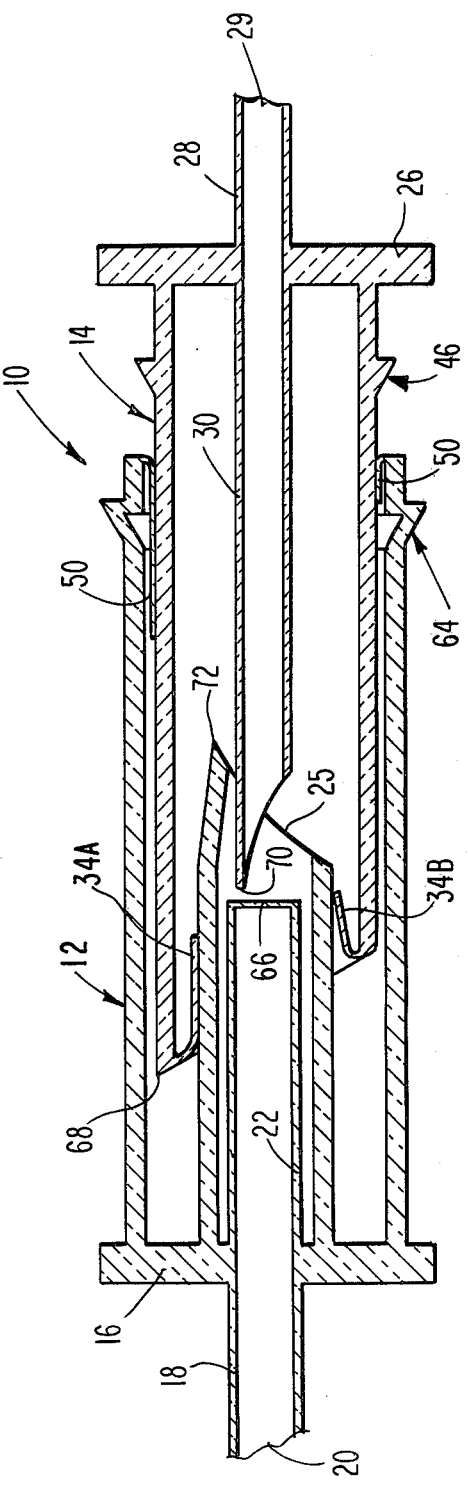

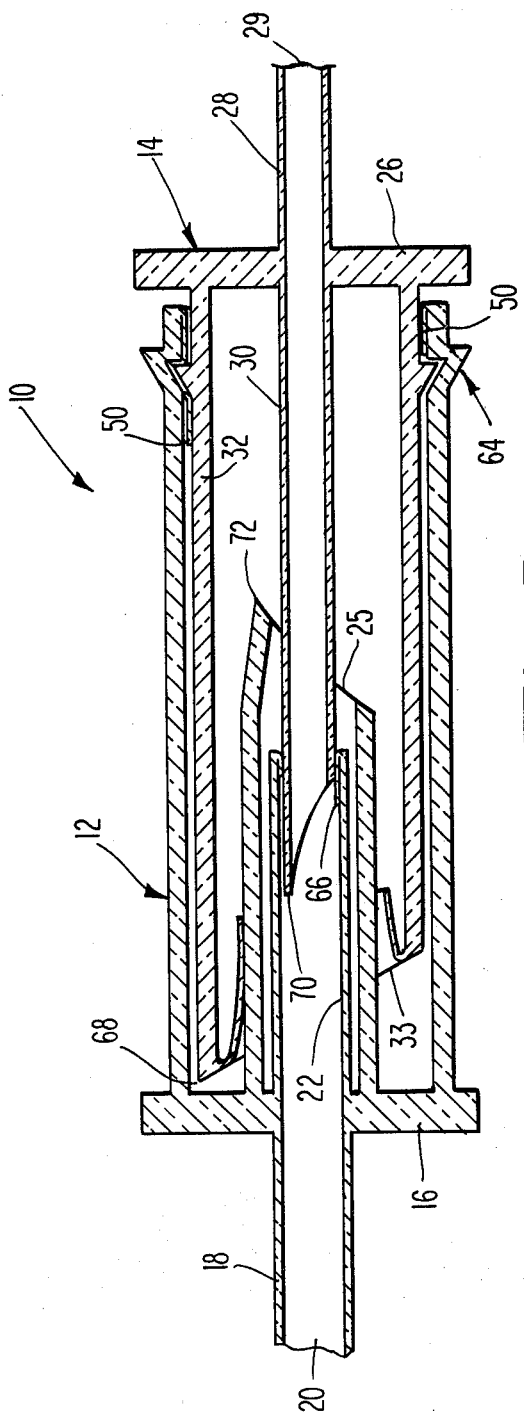
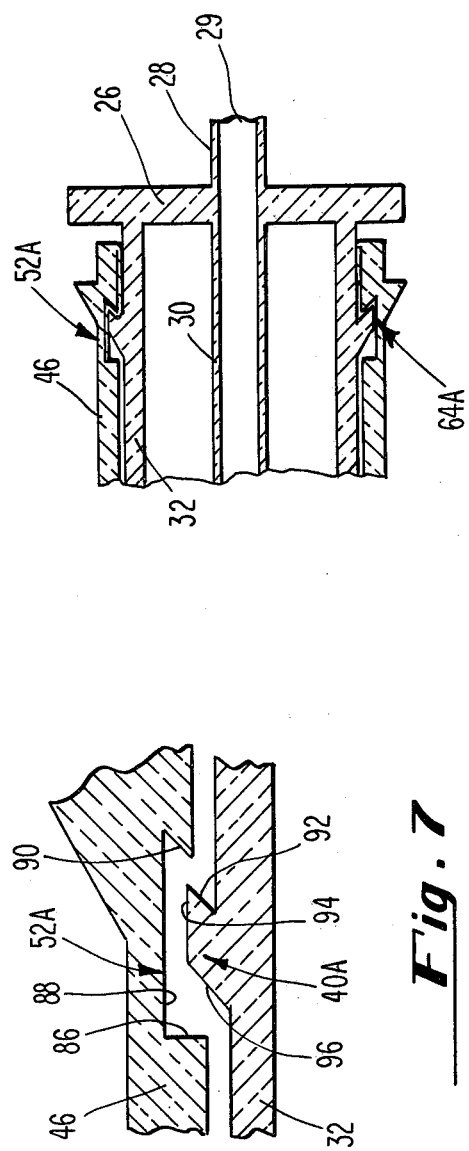

ASEPTIC CONNECTOR

BACKGROUND OF THE INVENTION

1. Field of the Invention

This invention relates to aseptic connectors for connecting two bodies, to create an aseptic juncture therebetween for flow of fluid from one body to another through the connector.

2. Description of the Prior Art

Aseptic connectors are well known; a variety of design approaches have been used in attempts to assure that when the connectors are used aseptic transfer of fluids results. The most popular approach has been to utilize membranes penetrated by a spike tip on the end of a tube receiving the fluid, as disclosed in U.S. Pat. No. 3,509,879. Aseptic connectors have also been provided with moveable interior probes, moved after the two parts of the connector are joined, to penetrate membranes disposed across the interior of one or both of the connector portions; see German Pat. No. 1,300,635 and U.S. Pat. No. 3,902,489. A variant of this approach is that disclosed in U.S. Pat. No. 3,986,508 wherein the members forming the connector are first partially joined, then sterilized, whereupon a seal, which assures the aseptic character of the connection, is broken.

Two problems are inherent in prior art connectors. First, if the spike used to penetrate the sealing membrane becomes contaminated before the membrane is broken, the spike may contaminate fluid passing through the connector. Slidably removable caps placed over spikes heretofore have not proved adequate to maintain the spikes in an aseptic condition since such caps may easily be accidently or intentionally removed by attendant personnel prior to the time for the connector to be used, wih contamination of the spike possibly resulting. The second problem is that in connectors in which a second action, such as moving a moveable probe, is required before fluid can flow through the connector after the connector has been joined, inattentiveness on the part of attendant personnel may result in the connector portions being structurally connected but, (due to failure by the attendant personnel to carry out the second step required when the connector portions are joined) no fluid flowing through the connector. These connectors which require two-stage operation have a further disadvantage in that they are expensive to fabricate since they cannot be injection molded in single or two-stage molding operations.

SUMMARY OF THE INVENTION

This invention provides a connector utilizing a spike to penetrate a membrane, where the spike is maintained in an aseptic environment substantially until the membrane is penetrated by tubular means surrounding the spike; only a single manual operation is required to affect the connection. The connector includes telescopingly engageable male and female elements having telescoping conduits extending from bases with annular walls surrounding the telescoping conduits through which fluid travels when the elements are engaged. Puncturable pellicular membranes at the extremities of the male and female elements maintain the element interiors (including the spike and the membrane it punctures) in an aseptic condition until the membranes are ruptured when the male and female elements are joined.

BRIEF DESCRIPTION OF THE DRAWINGS

FIG. 3 is a sectional view of male and female elements of a connector embodying the invention, with the male and female elements partially telescopingly engaged.

FIG. 4 is a sectional view of male and female elements of a connector embodying the invention, with the male and female elements telescopingly engaged to a greater degree than in FIG. 3.

FIG. 5 is a side sectional view of male and female elements of a connector embodying the invention, with the male and female elements fully telescopingly engaged.

FIG. 6 is a broken sectional view of a portion of male and female elements embodying the invention, illustrating alternative means for retaining the male and female elements in engagement.

FIG. 7 is an enlarged view of the portions of the male and female elements circled in FIG. 6.

DESCRIPTION OF THE PREFERRED EMBODIMENTS

Figure 1:
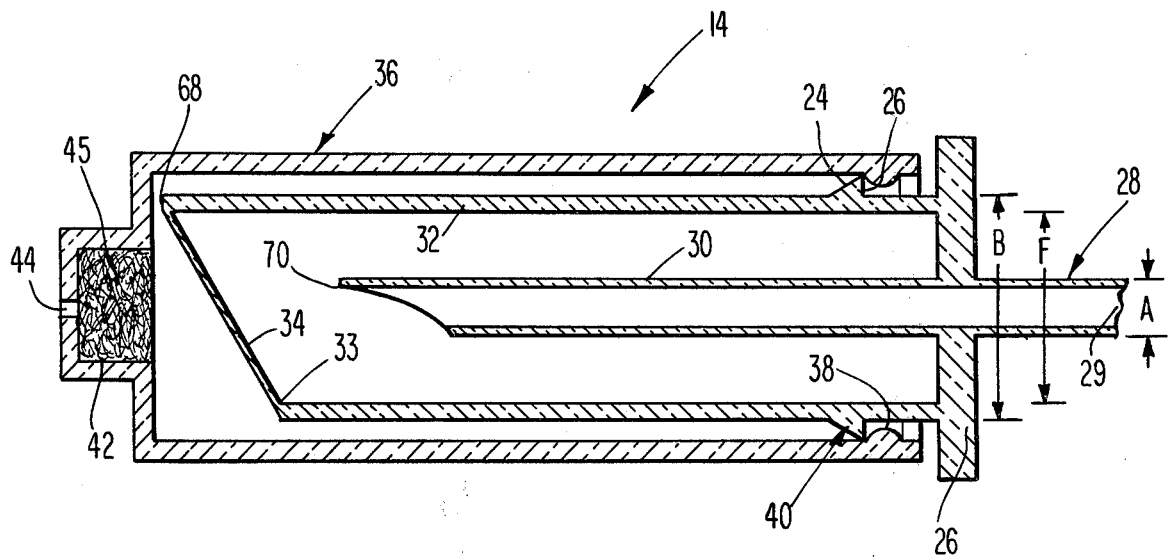
FIG. 1 is a sectional view of a male element portion of a connector embodying the invention, shown with a protective cap engaged thereover.

Referring to FIG. 1, the male element portion of the aseptic connector embodying the invention is designated generally 14 and includes a circular disk-like sole 26, a conduit (denominated as a second conduit to distinguish it from a conduit portion of a female element portion of the aseptic connector), designated 28 passing through sole 26, with a first end 29 of conduit 28 communicating with one of two bodies connected by the aseptic connector for flow of fluid therebetween. (Neither of the two bodies is shown in any of the drawings.) A second end 30 of conduit 28 extends distally from sole 26 and is telescopingly insertable into a first conduit of a female element portion of the aseptic connector of the invention. The distal extremity of second end 30 most remote from sole 26 is configured as a puncturing probe 70 for penetrating a sealing membrane and is formed by the opening to conduit 28 at second end 30 being skew to sole 26 and to the axis of symmetry of conduit 28. Extending from sole 26 is tubular means 32 which is concentrically spaced about second conduit 28 and extends from sole 26 a greater distance than second conduit 28. A pellicular membrane 34, arbitrarily designated as a second pellicular sealing membrane means, seals tubular means 32 at the end thereof remote from sole 26. The portion of tubular means 32 which is most remote from sole 26 is a puncturing probe 68 formed by distally extending end 33 of tubular means 32 being skew to sole 26 and to the axis of symmetry of conduit 28.

Also shown in FIG. 1 is a cap designated generally 36, which concentrically surrounds tubular means 32 and is retained in locking engagement therewith by a protruding circumferential bead 38 which interferes with a detent 40 extending from tubular means 32. Detent 40 is preferably annular about the exterior of tubular means 32 and has an angular surface portion 74, which flares away from the cylindrical exterior surface of tubular means 32, and a perpendicular surface portion 76, which extends away from the cylindrical exterior surface of tubular means 32 at a right angle thereto. Cap 36 has a recess 42 with a hole 44 therethrough to allow escape of air as cap 36 is inserted over male element 14. Cotton 62 within recess 42 prevents entry of contamination into the volume between cap 36 and male element 14 through hole 44. Cap 36 is manually removed from male element 14 prior to connection of male element 14 with a selected female element.

Figure 2:
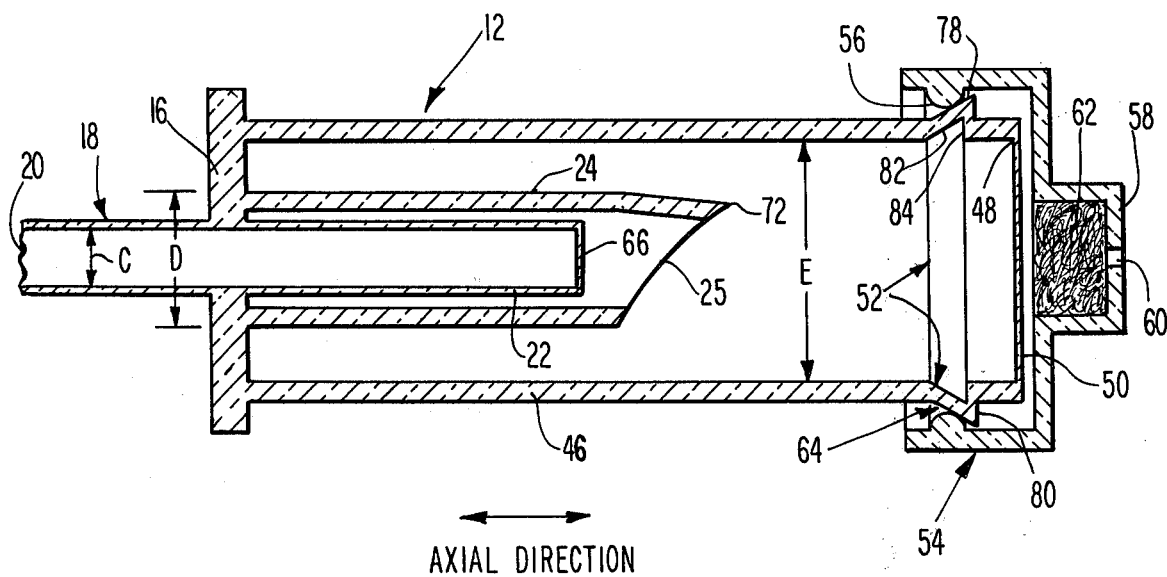
FIG. 2 is a sectional view of a female element portion of a connector embodying the invention, shown with a protective cap engaged thereover.

Referring to FIG. 2, a female element portion of the aseptic connector is designated generally 12 and includes a base 16, a first conduit 18 passing through base 16, with first conduit 18 having a first end 20 communicating with a first body, not shown, which is one of the bodies between which the aseptic connector effects fluid flow. First conduit 18 has a second end 22 extending distally from base 16. Female element 12 further includes a cylindrical sheath 24 extending from base 16 a greater distance than distally extending end 22 of first conduit 18, with cylindrical sheath 24 concentrically spaced about the portion of first conduit 18 which extends from base 16 and terminates as second end 22. Distal end 25 of sheath 24 has its opening formed skew to base 16 and to the axial direction; this effectively forms puncturing probe 72 at the extremity of distal end 25 most remote from base 16. An annular exterior wall 46 extends from base 16 a greater distance than, but in the same direction as, sheath 24 and is concentrically spaced about sheath 24 with a distal end of annular exterior wall 46 defining a first orifice 48. A pellicular membrane 50, arbitarily designated as a first pellicular sealing membrane means, provides means for sealing first orifice 48 at the distal end of annular exterior wall 46 remote from base 16.

Removed from first orifice 48 is an interior circumferential groove 52 formed by the interior of an angularly extending shoulder portion 64 of annular exterior wall 46. Groove 52 is formed such that the minimum diameter of the groove is closer to base 16 than is the maximum diameter of the groove. Groove 52 is configured angularly with respect to the axial direction to facilitate complemental locking engagement of the male and female elements of the connector when detent 40 on tubular means 32 of the male element of the connector fits into groove 52. Groove 52 is preferably annular about the interior of wall 46 and has an angular surface portion 82, which angles away from the cylindrical interior surface of wall 46, and a perpendicular surface portion 84, which extends outwardly from the cylindrical interior surface of wall 46 at a right angle thereto. The angle between surface portion 82 and wall 46 is preferably the same as the angle between angular surface portion 74 and the exterior surface of tubular means 32 of male element 14. The inner diameter of the portion of annular wall 46 between groove 52 and pellicular sealing means 50 is preferably slightly greater than the inner diameter of the portion of annular wall 46 between groove 52 and base 16, to allow detent 40 to easily reach groove 52 as the male element is inserted into the female element.

Still referring to FIG. 2, a cap 54 surrounds the distal end of female element 12 and is retained thereover by an annularly extending bead 56 within cap 54 which engages shoulder portion 64 of annular wall 46. Cap 54 has a recess 58 formed therein for receipt of cotton 62 which effectively seals hole 60 once cap 54 has been placed over female element 12. Hole 60 is necessary to allow escape of air as cap 54 is placed over the female element.

Second pellicular sealing membrane means 34 seals tubular means 32 of male element 14, at the end 33 of tubular means 32 remote from sole 26. First and third pellicular sealing membrane means 50 and 66 respectively seal the annular exterior wall distal end remote from base 16 of female element 12 and the second end 22 of first conduit 18 at the position remote from base 16 of female element 12. These three pellicular sealing means are sequentially punctured when the male and female element portions of the connector are telescopingly engaged with each other. Sequential rupturing of the pellicular sealing membranes assures that the interior portions of the connector male and female elements remain sterile until the male and female elements are telescopingly engaged for flow of fluid therethrough.

To facilitate the telescoping connection of the two elements, proper relationship must be maintained among the various tubular and cylindrically shaped members of the male and female elements. Specifically, outer diameter of tubular means 32 (of the male element), denoted by dimension B in FIG. 1, must be slightly less than inner diameter of annular exterior wall 46 (of the female element), denote by dimension E in FIG. 2. Similarly, outer diameter of second end 30 of second conduit 28 (of the male element), denoted by dimension A in FIG. 1, must be less than inner diameter of second end 22 of first conduit 18 (of the female element), denoted by dimension C in FIG. 2. Moreover, outer diameter of sheath 24 (of the female element), denoted by dimension D in FIG. 2, must be less than inner diameter of tubular means 32 (of the male element), denoted by dimension F in FIG. 1. Of course, the elements are constructed so that they fit closely together, in sliding, telescopic fashion, to assure that there is no chance for contamination of the fluid passing therethrough once connection between the male and female elements is affected.

When the connector is assembled into operative disposition by inserting male element 14 into female element 12, puncturing probe 68 of tubular means 32 initially punctures pellicular sealing membrane means 50. Pellicular means 50 separates into two portions 50A and 50B, as best shown in FIG. 3. As the two elements are further urged together, second pellicular sealing means 34 encounters puncturing probe 72 of sheath 24 and is punctured thereby. Second pellicular sealing membrane 34 ruptures into two parts, 34A and 34B, as best shown in FIG. 4. As sole 26 is further urged towards base 16, the elements become further engaged, with puncturing probe 70 of second conduit 28 rupturing third pellicular sealing means 66, affecting connection between first conduit 18 and second conduit 28 thereby affecting connection of the two bodies for flow of fluid therebetween. As the elements are finally engaged, detent 40 interferes with the inner surface of annular wall 46 until detent 40 resides in groove 52. This is best shown in FIG. 5. Once detent 40 has found groove 52, perpendicularly extending portion 76 of detent 40 contacts perpendicular bottom portion 84 of groove 52, thereby preventing the male and female elements from becoming disengaged. The cross-sectional configuration of groove 52 is preferably of the same shape, and only slightly larger than, the cross-sectional configuration of detent 40, so that detent 40 will fit securely in groove 52 thereby preventing the elements from becoming disengaged.

An alternate configuration for the groove and detent is illustrated in FIGS. 6 and 7 where the detent is designated 40A and the groove is designated 52A. Other than the configuration of the groove and detent, the male and female elements are substantially the same as shown in FIGS. 1 through 5 with tubular means 32, sole 26, second conduit 28, first and second ends 29 and 30 of second conduit 28 and annular exterior wall 46 all being so designated in FIGS. 6 and 7. In the configuration shown in FIGS. 6 and 7, groove 52A consists of a perpendicular portion 86, which is perpendicular with respect to the cylindrical interior of annular exterior wall 46, a parallel annular portion which is parallel with respect to the cylindrical interior of annular wall 46 and an angular portion which makes an angle with respect to the cylindrical interior of annular wall 46. Angular portion 90 interacts with a first angular portion 92 of detent 64A to prevent the male and female elements from disengaging. Detent 64A in the configuration shown consists of a first angular portion, which is angular with respect to the cylindrical exterior of tubular means 32, which is more proximate sole 26 than the remainder of detent 64A. Detent 64A further comprises a parallel portion 94, which is parallel with respect to the cylindrical exterior of tubular means 32, and a second angular portion 96, which is more remote from sole 26 than is first angular portion 92, and which is also angular with respect to the cylindrical exterior of tubular means 32.

As in the first embodiment, the inner diameter of the portion of annular wall 46 between groove 52A and pellicular sealing means 50 is preferably slightly greater than the inner diameter of the portion of annular wall 46 between groove 52A and base 16, to allow detent 40A to easily reach groove 52A as the male element is inserted into the female element.

The elements of the connector are preferably fabricated from plastic, preferably by injection molding. The pellicular sealing membranes may be molded in place, in a multistage molding operation, or may be affixed by heat sealing or with a suitable adhesive.

Variations and combinations, including reversals of parts from those shown and other modifications, all fall within the scope of this invention. The above description is by way of the illustration and not by way of limitation. Changes, omissions, additions, substitutions, and/or other modifications may be made without departing from the spirit of the invention.

I claim the following:

1. An aseptic connector for affecting aseptic juncture of two bodies, for fluid flow therebetween, through said connector, comprising:
   (a) a female element including:
      (i) a base;
      (ii) a first conduit passing through said base, a first end thereof communicating with said first body, a second end thereof extending distally from said base;
      (iii) a cylindrical sheath extending from said base a greater distance than said second end of said first conduit, concentrically spaced about said distally extending second end of said first conduit;
      (iv) an annular exterior wall extending from said base a greater distance than said sheath, concentrically spaced about said sheath, a distal end of said exterior wall defining a first orifice; and
      (v) first pellicular means for sealing said first orifice at said annular exterior wall distal end;
   (b) a male element, telescopingly engageable with said female element, including:
      (i) a sole;
      (ii) a second conduit passing though said sole, a first end thereof communicating with said second body, a second end thereof extending distally from said sole, said second conduit telescopingly insertable into said first conduit;
      (iii) tubular means extending from said sole a greater distance than said second conduit, concentrically spaced about said second conduit, having an outer diameter less than inner diameter of said annular wall, said tubular means telescopingly insertable into said annular exterior wall; and
   (c) means for retaining said male and female elements in telescoping engagement, with said tubular means at least partially resident within said annular exterior wall and said second conduit at least partially resident within said first conduit.

2. The connector of claim 1 further comprising second pellicular means for sealing said tubular means remote said sole.

3. The connector of claim 2 further comprising third pellicular means for sealing said second end of said first conduit.

4. The connector of claim 1 wherein a distal end of said tubular means, remote said sole, is a puncturing probe for said first pellicular means and is skew with respect to said sole.

5. The connector of claim 2 wherein a distal end of said sheath, remote said base, is a puncturing probe for said second pellicular means and is skew with respect to said base.

6. The connector of claim 1 wherein said retaining means further comprises:
   (a) a circumferential groove within said annular exterior wall; and
   (b) a protruding detent, configured for complemental engagement with said groove, about said tubular means exterior, when said male and female elements are telescopingly engaged.

7. The connector of claim 6 wherein said groove has a bottom portion more remote from said base than a vertex portion of said groove, to retain said detent within said notch upon insertion of said tubular means into said annular exterior wall.

8. The connector of claim 6 wherein said detent extends circumferentially around said tubular means exterior.

9. The connector of claim 6 wherein said detent includes a portion perpendicular to said tubular means exterior and proximate said sole and said notch includes a detent receiving portion perpendicular to said annular exterior wall.

10. The connector of claim 6 wherein said detent tapers along a surface from said tubular means exterior to a vertex.

* * * * *